(12) United States Patent
Kobuke et al.

(10) Patent No.: US 6,727,358 B2
(45) Date of Patent: Apr. 27, 2004

(54) PORPHYRIN ARRAY HAVING IMIDAZOLYL PORPHYRIN METAL COMPLEX AS STRUCTURAL UNIT THEREOF AND METHOD OF PRODUCING THE SAME

(75) Inventors: Yoshiaki Kobuke, Ikoma (JP); Kazuya Ogawa, Ikoma (JP)

(73) Assignee: Nara Institute of Science and Technology, Ikoma (JP)

( * ) Notice: Subject to any disclaimer, the term of this patent is extended or adjusted under 35 U.S.C. 154(b) by 25 days.

(21) Appl. No.: 10/231,074

(22) Filed: Aug. 30, 2002

(65) Prior Publication Data

US 2003/0187251 A1 Oct. 2, 2003

(30) Foreign Application Priority Data

Feb. 1, 2002 (JP) .................................... 2002-025983

(51) Int. Cl.[7] ........................................... C07D 487/22
(52) U.S. Cl. ...................................... 540/145; 540/121
(58) Field of Search .................... 540/145, 121

(56) References Cited

U.S. PATENT DOCUMENTS 6,429,310 B2   8/2002   Kobuke et al. ............. 540/145

OTHER PUBLICATIONS

M. Terazima, et al., J. Appl. Phys., vol. 81, No. 7, pp. 2946–2951, "The Third–Order Nonlinear Optical Properties of Prphyrin Oligomers", Apr. 1, 1997.

Kazuya Ogawa, et al., "Large Third–Order Optical Nonlinearity of Self–Assembled Porphyrin Oligomers", J. Am. Chem. Soc., vol. 124, No. 1, (2002).

*Primary Examiner*—John M. Ford
(74) *Attorney, Agent, or Firm*—Oblon, Spivak, McClelland, Maier & Neustadt, P.C.

(57) ABSTRACT

A porphyrin array represented by the following general formula (1-1) or (1-2):

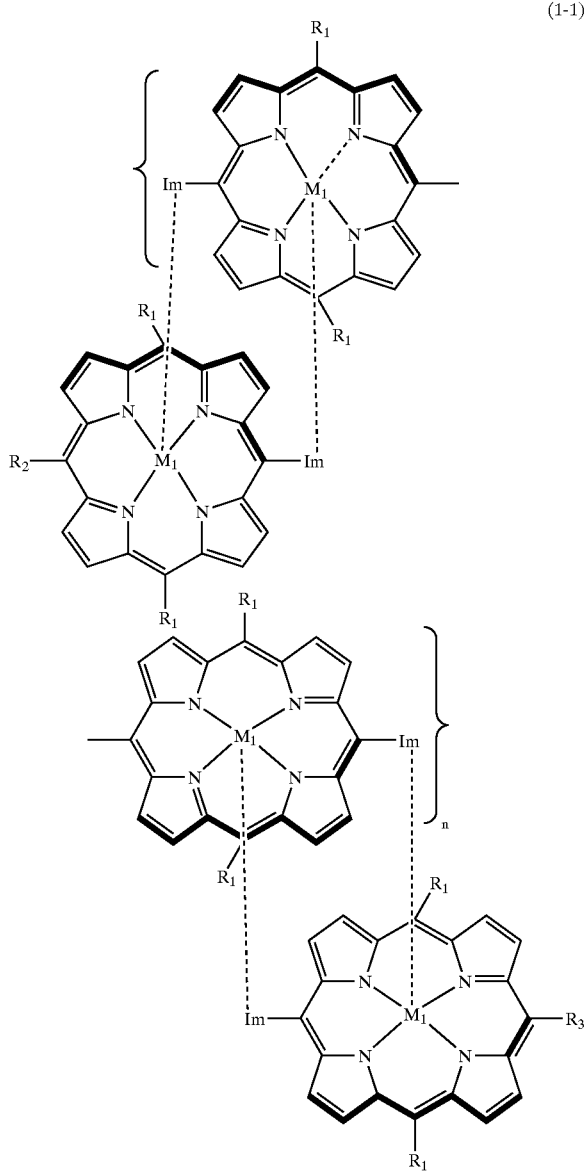

(1-1)

Gel permeation chromatogram

-continued (1-2)

wherein $R_1$ represents an alkyl group or a substituted or unsubstituted aryl group; $M_1$ represents a metal ion; $R_2$ and $R_3$ independently represent an electron acceptor or an electron donor; Im represents $Im_1$ or $Im_2$ set forth below:

wherein $R_4$ represents a hydrogen atom or a methyl group; and n represents an integer in the range of 1 to 100.

18 Claims, 1 Drawing Sheet

PORPHYRIN ARRAY HAVING IMIDAZOLYL PORPHYRIN METAL COMPLEX AS STRUCTURAL UNIT THEREOF AND METHOD OF PRODUCING THE SAME

CROSS-REFERENCE TO RELATED APPLICATIONS

This application is based upon and claims the benefit of priority from the prior Japanese Patent Application No. 2002-25983, filed Feb. 1, 2002, the entire contents of which are incorporated herein by reference.

BACKGROUND OF THE INVENTION

1. Field of the Invention

The present invention relates to a novel material exhibiting a third-order nonlinear optical property. More specifically, the present invention relates to a porphyrin array having bis(imidazolyl porphyrin metal complex) as structural unit thereof, which array exhibiting excellent third-order nonlinear optical properties.

2. Description of the Related Art

A third-order nonlinear optical material is essentially required for the development of optical fast optical switch and an optical modulation element. However, in order to employ such a third-order nonlinear optical material in actual applications, it is considered that the performance of the material, converted and expressed as the value of third-order susceptibility ($\chi^{(3)}$), must be enhanced by the order of three digits or so, as compared with the organic materials which have been reported. When an organic compound exhibiting significant nonlinearity is designed, it is important that the polarizability of the molecule is increased by increasing the degree of overlap of the orbitals by expanding the $\pi$ electron conjugate system, and by combining an electron donor with an electron acceptor.

Porphyrin is a cyclic tetrapyrrole in which four pyrrole nucleuses are alternatively bridged by four methine groups and has a large conjugate system constituted of $18\pi$ electrons. Due to this, porphyrin has been studied as a nonlinear optical material. In the conventional study, Anderson reported that the one-dimensional linear porphyrin array, in which free base or metalloporphyrins are connected to each other with butadiyne bonds, exhibits more large nonlinearity, as compared with the porphyrin complex monomer (Chem. Phys., 248, 181 (1999)). However, in this case, the length of the resulting polymer cannot be regulated due to the use of tile covalent bonds. Further, as neither introduction of a hetero metal thereto nor introduction of a donor or acceptor at the terminal substituent thereof is easy, the nonlinear property of the resulting polymer cannot be improved any further. On the other hand, Osuka et al. synthesized a one-dimensional linear porphyrin array in which free base or metalloporphyrins are directly connected to each other at the meso position thereof and a one-dimensional linear porphyrin array in which the porphyrin complexes are bridged to each other with phenylene groups, and measured the degree of nonlinearity of the synthesized porphyrin structures. However, as the donor or acceptor is not introduced thereto, the resulting polymer of Osuga et al. failed to exhibit a significantly large nonlinear property (J. Appl. Phys., 81, 2946 (1997)). In short, it is difficult, by using a covalent bond, to introduce a donor and an acceptor which should provide a high polarizability to a one-dimensional linear porphyrin array. Therefore, significantly large nonlinear property cannot be realized by the conventional method of synthesizing a porphyrin array.

BRIEF SUMMARY OF THE INVENTION

An object of the present invention is to provide a material that exhibits a third-order nonlinear optical response of a significantly large magnitude.

Another object of the present invention is to provide a method of producing such a material.

In order to attain the objects described above, the inventors of the present invention synthesized a novel porphyrin dimer consisting of a metal complex of porphyrin having an imidazolyl group and porphyrin having an imidazolyl group but no metal (hereinafter this dimer is referred to as a mono-metal porphyrin complex dimer). The inventors found that the mono-metal porphyrin complex dimer can be a terminal molecule of the porphyrin array, and serves as an electron donor and acceptor. Specifically, the metal complex of porphyrin having an imidazolyl group serves as a donor and the porphyrin having an imidazolyl group but no metal serves as an acceptor.

The inventors had discovered, prior to the synthesis of the mono-metal porphyrin complex dimer described above, that by coordinating a nitrogen atom of an imidazolyl group of one imidazolyl porphyrin metal complex to the metal atom of another imidazolyl porphyrin metal complex, thereby forming bridges between the porphyrin complexes, a porphyrin array in which a plurality of imidazolyl porphyrin complex dimers are connected to each other by way of coordinate bonds, can be obtained (hereinafter, the diner consisting of two porphyrin complexes are also referred to as bis-porphyrin complex diner). The inventors also discovered that, in a reaction system, the coordinate bonds of the porphyrin array can be cleaved and reconstructed by adding and removing a solvent, such as methanol or pyridine, respectively (JP-A 2001-213883, which corresponds to the allowed U.S. application Ser. No. 09/767,900, and JP-A 2001-253883, which corresponds to a co-pending application Ser. No. 09/802,923).

The inventors found that a mixture of the newly synthesized mono-metal porphyrin complex dimers and a porphyrin array having, as its structural unit, bis-porphyrin complex dimers, may be re-organized in a polar solvent, such as methanol or pyridine, thereby a material exhibiting a significantly large nonlinear optical response can be formed, and accomplished the present invention.

Accordingly, the present invention provides a porphyrin array represented by the following general formula (1-1) or (1-2):

(1-1)

-continued (1-2)

wherein $R_1$ represents an alkyl group or a substituted or unsubstituted aryl group; $M_1$ represents a metal ion;

$R_2$ and $R_3$ independently represent an electron acceptor or an electron donor, preferably selected from the group consisting of free base porphyrin, gold porphyrin, pyromellitic diimide, dialkylviologen, benzoquinone and ferrocene; Im represents $IM_1$ or $Im_2$ shown below:

wherein $R_4$ represents a hydrogen atom or a methyl group); and n represents an integer in the range of 1 to 100.

The present invention also provides a method of producing the porphyrin array represented by the general formula (1-1) or (1-2) of the present invention comprising:

reacting, in the presence of a polar solvent, either one or both of porphyrin metal complexes represented by the general formulae (2-1) and (2-2):

(2-1)

(2-2)

wherein $R_1$, $R_2$, $R_3$, $M_1$ and Im have the same meanings as in the general formula (1-1) or (1-2) with bis-porphyrin complex dimer represented by the general formula (3):

(3)

wherein $R_1$, $M_1$ and Im have the same meanings as in the general formula (1-1).

As an example of the porphyrin metal complex represented by the general formula (2-1) or (2-2), a nono-metal porphyrin complex dimer represented by the general formula (2') may be used:

(2')

wherein $R_1$, $M_1$ and Im have the same meanings as in the general formulae (1-1).

The porphyrin array represented by the general formula (1-2) may be synthesized by reacting, in the presence of a polar solvent, either one of both of the porphyrin metal complexes represented by the general formulae (2-1) and (2-2). The present invention also provides this method of preparing the porphyrin array represented by the general formula (1-2).

The present invention also provide the porphyrin metal complex represented by the general formula (2-1) or (2-2).

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

The porphyrin array represented by the general formula (1-1) of the present invention will be described in detail below. The following description regarding the general formula (1-1) of the present invention are also applied to the porphyrin array represented by the general formula (1-2) of the present invention, unless otherwise indicated.

In the general formula (1-1) described above, $R_1$ represents an alkyl group or a substituted or unsubstituted aryl group.

Examples of the alkyl group represented by $R_1$ include linear, branched and cyclic alkyl groups. The number of the carbon atom of the alkyl group represented by $R_1$ is not particularly limited as long as the porphyrin array of the present invention can be used as a third-order nonlinear optical material. The number of the carbon atom of the alkyl group is preferably 1–20, and more preferably 5–20, in view of the advantages in the production process and solubility and the like.

The alkyl group represented by $R_1$ may have a substituent, as long as the porphyrin array of the present invention can be used as a third-order nonlinear optical material.

The aryl group represented by $R_1$ may be either substituted or unsubstituted. The substituent of the substituted aryl group is not particularly limited, as long as the porphyrin array of the present invention can be used as a third-order nonlinear optical material. Specific examples of the substituent of a substituted aryl group represented by $R_1$ include an alkyl group and an alkoxy group. The number of the alkyl group and the alkoxy group, and the position of the substituent, are not particularly limited. However, for making the production easier and obtaining high solubility, the number of the substituent is preferably 1–3. The position of the substituent may be, with regard to the bonding to porphyrin, at any of ortho-, meta- and para-positions. In view of advantages in the production process and the like, the substituted aryl group represented by $R_1$ is most preferably an aryl group substituted with one alkoxy group at the para-position.

The number of the carbon atom of the aryl group represented by $R_1$ is not particularly limited, as long as the porphyrin array of the present invention can be used as a third-order nonlinear optical material. In the case where $R_1$ is an unsubstituted aryl group, the number of the carbon atom of the aryl group represented by $R_1$ is preferably 6–20, and more preferably 6. In the case where $R_1$ is an aryl group substituted with an alkyl group or an alkoxy group, the total number of the carbon atom (including that of the substituent) is preferably 7–30, and more preferably 7–24.

In terms of solubility of the porphyrin array, $R_1$ is preferably an alkyl group, an aryl group substituted with an alkyl group, or an aryl group substituted with an alkoxy group.

In the general formula (1-1), a plurality of $R_1$ groups may be the same or different. However, in order to make the production easier, it is preferable that the $R_1$ groups are the same.

In the general formula (1-1), $R_2$ and $R_3$ independently represent an electron acceptor or electron donor. $R_2$ and $R_3$ may be the same or different. However, $R_2$ and $R_3$ groups are preferably the same for production easiness. The type of the electron acceptor and the type of the electron donor are not particularly limited, as long as the porphyrin array of the present invention has a third-order nonlinear optical property. Examples of the electron acceptor include, but are not limited to, free base porphyrin, Au(III) porphyrin, pyromellitic diimide, dialkylviologen, and benzoquinone, from all of which a hydrogen atom is removed thereby becoming a monovalent group. Examples of the electron donor include, but are not limited to, a monovalent group obtained by removing one hydrogen atom from ferrocene. Specific examples of the electron acceptor and the electron donor of the present invention are shown below, however, the electron acceptor and the electron donor of the present invention are not limited to these specific examples:

-continued

, and wherein $R_1$ has the same meaning as in the general formula (1-1); $R_5$ and $R_7$ independently represent an alkylene group or arylene group; and $R_6$ and $R_8$ independently represent an alkyl group or aryl group. In the above examples of an electron donor or acceptor, a plurality of $R_1$ groups in one porphyrin monomer may be the same or different. However, in order to make the production easier, it is preferable that the $R_1$ groups are the same.

Examples of the alkylene group represented by $R_5$ and $R_7$ include linear, branched and cyclic alkylene groups. The number of the carbon atom of the alkylene group represented by $R_5$ and $R_7$ is not limited, as long as the porphyrin array of the present invention has a third-order nonlinear optical property. However, for production easiness and the like, the number of the carbon atom of the alkylene group is preferably 1–20, and in consideration of the strength of the acceptor and the like, 1–5 is more preferable.

The number of the carbon atom of the arylene group represented by $R_5$ and $R_7$ is not limited, as long as the porphyrin array of the present invention has a third-order nonlinear optical property. However, for the production easiness and the like, the number of the carbon atom of the arylene group is preferably 6–20, and more preferably 6.

The alkylene and arylene groups represented by $R_5$ and $R_7$ may have a substituent, as long as the porphyrin array of the present invention has a third-order nonlinear optical property.

Examples of the alkyl group represented by $R_6$ and $R_8$ include linear, branched and cyclic alkyl groups. The number of the carbon atom of the alkyl group represented by $R_6$ and $R_8$ is not limited, as long as the porphyrin array of the present invention has a third-order nonlinear optical property. However, in consideration of the solubility and the like, the number of the carbon atom of the alkyl group is preferably 1–20, and more preferably 1–8.

The number of the carbon atom of the aryl group represented by $R_6$ and $R_8$ is not limited, as long as the porphyrin array of the present invention has a third-order nonlinear optical property. However, in consideration of the advantages in the production process and the like, the number of the carbon atom of the aryl group is preferably 6–20, and more preferably 6.

The alkyl and aryl groups represented by $R_6$ and $R_8$ may have a substituent, as long as the porphyrin array of the present invention has a third-order nonlinear optical property. Examples of such substituent include, but are not limited to, an alkoxycarbonyl group and alkyl-substituted naphthalene diimide.

In the general formula (1-1), as the electron acceptor or the electron donor of $R_2$ and $R_3$, pyromellitic diimide represented by the following formula:

wherein $R_5$ and $R_6$ are as defined above, is preferable in terms of the advantages in production.

In the general formula (1-1), Im represents $Im_1$ or $Im_2$:

wherein $R_4$ represents a methyl group or a hydrogen atom. In the formulae, each arrow indicates a coordination site to the metal represented by $M_1$.

In the general formula (1-1), Im may be either $Im_1$ or $Im_2$, but $R_4$ is preferably a methyl group, in consideration of the coordination force with respect to the metal ion.

In the general formula (1-1), n represents an integer of 1 to 100, but n may exceed 100 depending on the use of the porphyrin array. In the formula (1-1), the value of n may be set, in an appropriate manner, in accordance with the type of the third-order nonlinear optical material for which the porphyrin array of the present invention to be used (e.g., an ultra fast optical switch and an optical modulation element).

The porphyrin array represented by the general formula (1-2) is that having the smallest number of the structural unit within the scope of the invention.

As described above, the porphyrin array of the present invention is an oligomer or polymer comprising one or more porphyrin metal complex dimers, at both ends of which are terminated with porphyrin that can no longer extend the array. The porphyrin metal complex dimer is constituted of two porphyrin metal complexes. In the dimer, the 5-position of one porphyrin metal complexes is bonded to 5'-position of another porphyrin metal complex. In the dimer, the plane defined with one porphyrin metal complex is approximately perpendicular to the plane defined with the other porphyrin metal complex. At each of the 15- and 15'-positions an imidazolyl group represented by Im is attached. The imidazolyl group is attached to the porphyrin ring so that the plane defined with the imidazolyl ring is approximately perpendicular to the plane defined with the porphyrin ring. At each of the 10-, 10'-, 20- and 20'-positions, a substituent represented by $R_1$ is attached.

In the porphyrin array, there are two coordinate bonds connecting each of the porphyrin metal complex dimers. One coordinate bond is formed between the imidazolyl group (Im) of one dimer and the central metal ion ($M_1$) of adjacent dimer, and the other coordinate bond is formed between the central metal ion ($M_1$) of the former dimer and the imidazolyl group (Im) of the latter dimer.

The porphyrin array of the present invention having the above-mentioned structural features can be a material having a significant third-order nonlinear optical property, due mainly to the terminal porphyrins each serving as an electron acceptor or donor. The magnitude of the nonlinear response exhibited by the porphyrin array of the invention is approximately one-digit larger than that of the reference compound having no an acceptor or donor at the terminals thereof.

A method of synthesizing the porphyrin array represented by the general formulae (1-1) and (1-2) of the present invention will be described in detail below, but the present invention is not limited to this method.

The porphyrin array represented by the general formula (1-1), wherein $R_2$ and $M_1$ are free base porphyrin and Zn (II), respectively, may be synthesized through Steps I–III set forth below.

<Step I> Synthesis of Compound II (General Formula (2-1), Wherein $R_2$ and $M_1$ are Free Base Porphyrin and Zinc, Respectively.)

(wherein $R_1$ and Im have the same meanings as defined in the general formula (2-1))

One porphyrin of the bis-free base porphyrins of Compound I is converted into a zinc complex. This conversion can be effected by dissolving Compound I in a solution to which Compound I is soluble, such as chloroform or dichloromethane, and then adding a zinc (II) salt, such as zinc acetate to the mixture.

The amount of zinc acetate to be added may be set at 1–2 times as much as the weight of Compound I. The reaction temperature is usually set at room temperature (approximately 25° C. to 30° C.). The reaction time or period is usually set in the range of 0.5 to 3 hours.

After the reaction, the reaction solution is washed with distilled water and the organic layer is concentrated under a reduced pressure. The residue is purified by using gel permeation chromatography (GPC), whereby Compound II is obtained. Compound II exhibits, in chloroform, the structure of Compound IV (general formula (1-2), wherein $R_2=R_3=$free base porphyrin, and $M_1=$zinc).

<Step II> Synthesis of Compound III

(wherein $R_1$ and Im have the same meanings as defined in the general formula (2-1))

Both porphyrins of the bis-free base porphyrins of Compound I are converted into zinc complexes. This conversion can be effected by dissolving Compound I into a non-polar solvent such as chloroform or dichloromethane, and then adding zinc (II) salt, such as zinc acetate thereto.

The amount of zinc acetate to be added may be set at 5 to 100 times as much as the weight of Compound I. The reaction temperature is usually set at room temperature (approximately 25° C. to 30° C.). The reaction time or period is usually set in the range of 0.5 to 3 hours.

After the reaction, the reaction solution is washed with distilled water and the organic layer is concentrated under a reduced pressure. Compound III is in the forms of porphyrin array in a non-polar solvent.

<Step III> Synthesis of the Porphyrin Arrays, Compound IV and Compounds V(n)

II

+

III pyridine
evaporation
<Step III>

IV

+

V(n)

(wherein $R_1$ Im and n have the same meanings as defined in the general formula (1-1))

Compound II and Compound III are dissolved into a polar solvent, such as pyridine, and mixed. The molar ratio of Compound II to Compound III may be 2:1 to 2:n, wherein n is an integer of 1 to 100. The reaction temperature is usually set at room temperature (approximately 25° C. to 30° C.). The reaction time or period is usually set at 0.5 hour. After the reaction, the solvent is removed under a reduced pressure to obtain a mixture of Compound IV and Compounds V(n).

The thus obtained mixture may be separated into each compound by GPC using a solvent such as chloroform as an eluting solvent. In the column for GPC, polystyrene may be usually used as the packing material.

The porphyrin array represented by the general formula (1-2), as one of the components of the mixture, may be obtained in accordance with the above method comprising Steps I to III. The porphyrin array represented by the general formula (1-2) alone may be obtained in the same manner as the above method comprising Steps I to III, except that only the compound represented by the general formula (2-1) and/or the compound represented by the general formula (2-2) are used, without using the compound represented by the general formula (3).

The following Steps IV and V are examples of synthesizing porphyrins having pyromellitic diimide as $R_2$ and zinc as $M_1$, respectively, to be used as the terminal porphyrin of the porphyrin array of the invention represented by the general formula (1-1) or (1-2).

<Step IV> Synthesis of Compound XII

IX

+ Im—CHO +

X

XII (wherein $R_1$ and Im have the same meanings as defined in the general formula (1-1).)

Compound IX, Compound X and Compound XI are dissolved into a solvent to which these starting compounds are soluble, such as $CHCl_3$ or acetonitrile, and the atmosphere was substitution with the nitrogen atmosphere. Thereafter, TFA (trifluoroacetic acid) is added to the mixture to obtain Compound XII.

The amounts of Compound IX, Compound X and Compound XI to be added are usually set so that the ratio of the amounts is in the range of 4:1:2 to 3:1:2. The starting materials, including Compound IX, can be commercially available or synthesized by one skilled in the art according to methods described in literatures.

The amount of the solvent is usually set at 500–1000 times as much as the weight of Compound XI. The reaction temperature is usually set in the range of 20° C. to 30° C. The reaction time is usually set in the range of 30 to 120 minutes.

After the reaction, further processes such as purification may optionally be carried out. Then, the obtained substances are treated in the next <Step V>. The purification process can be carried out, for example, by evaporating the solvent used in the aforementioned reaction, dissolving the remaining mixture into a solvent, such as chloroform or dichloromethane, adding an aqueous solution of sodium bicarbonate to the obtained solution, separating the organic layer therefrom, drying the organic layer to concentrate, and effecting purification by using silica gel column chromatography or the like.

<Step> Synthesis of Compound XIII

XII

XIII (wherein $R_1$ and Im have the same meanings as defined in the general formula (1-1).)

Compound XII obtained in Step IV described above is converted into a zinc complex XIII. This reaction can be effected by dissolving Compound XII into a non-polar solvent, such as chloroform or dichloromethane, and then adding zinc acetate (II) thereto.

The amount of zinc acetate to be added is usually set at $5 \geqq 20$ times as much as the weight of Compound XII.

The reaction temperature is usually set at room temperature (approximately 25° C. to 30° C.). The reaction time is usually set in the range of 1 to 3 hours.

After that, the reaction solution is washed with distilled water and the organic layer is concentrated under a reduced pressure. The residue is purified by using silica gel chromatography, whereby Compound XIII is obtained.

In the method of the present invention, the value of n in the general formula (1-1) may be arbitrarily selected by changing the number of the structural unit of the bisporphyrin complex dimer to be used, the polarity, concentration and the temperature of the solvent to be used in the reaction, and the like.

EXAMPLES

Example 1

The porphyrin array of the present invention and the method of preparing the porphyrin array will be described in more detail by the following examples, but the present invention is not limited to these examples.

1) Step 1

Synthesis of 15,15'-bis(1-methyl-2-imidazolyl)-10,10', 20,20'-tetrakisheptyl-5,5'-bisporphyrin mono-zinc complex (2); in the formula of Compound II described above, Im represents $Im_1$, wherein $R_4$ is a methyl group, and $R_1$ represents a heptyl group.

25 μmol of 15,15'-bis(1-methyl-2-imidazolyl)-10,10', 20,20'-tetrakisheptyl-5,5'-bisporphyrin (1) was dissolved into 3 mL of chloroform. 0.2 mL of a methanol solution saturated with zinc acetate was added to the mixture, and stirred for 30 minutes at room temperature. The chloroform solution was washed with water. After the solvent was evaporated, the residue was purified with gel permeation chromatography (GPC), using chloroform as the developing solvent thereby to obtain 12.5 μmol (yield: 50%) of the title compound. MS(TOF)m/e 1235.08(M+1), Calc. 1234.98(M+1); Ultraviolet-visible absorption spectrum ($CHCl_3$) $\lambda_{max}$415, 468, 525, 575, 620, 655 nm; Fluorescence spectrum ($CHCl_3$) $\lambda_{max}$680 nm($\lambda_{ext}$420 nm); $^1$H NMR($\delta$:$CDCl_3$) −1.94 (NH, s, 4H), 0.90($CH_3$, t), 1.32($CH_2$, q), 1.94($CH_3$ (Im), s, 6H), 2.44($CH_2$, q, 4H), 2.75($CH_2$, q, 8H), 2.90($CH_2$, q, 4H), 3.21(Im-4, s, 2H), 3.58($CH_3$(Im'), s, 6H), 4.82($CH_2$, m, 4H), 5.14($CH_2$, m, 12H), 5.76((13, 17, d—d, 4H), 6.02(Im-5, s, 2H), 7.45(2, d, 2H), 7.59(Im-4', s, 2H), 7.81 (Im-5', s, 2H), 8.15(7', d, 2H), 8.33(3', d, 2H), 8.87(12', 18', d, 4H), 8.98(8, d, 2H), 9.08(12, 18, d, 4H), 9.33(2', d, 2H), 9.39(8', d, 2H), 9.47(13', 17', d—d, 4H), 9.61(7, d, 2H), 9.65(3, d, 2H).

Compound (2) in chloroform is in the form of Compound (4) (general formula (1-2), wherein $R_1$=heptyl, $R_2$=$R_3$=free base porphyrin, and Im=$Im_1$ ($R_4$=methyl). Accordingly, the data of ultraviolet-visible absorption spectrum, fluorescent spectrum, and $^1$H NMR spectrum were obtained as the data of Compound (4).

2) Step 2

Synthesis of 15,15'-bis(1-methyl-2-imidazolyl)-10,10', 20,20'-tetrakisheptyl-5,5'-bisporphyrin bis-zinc complex (3); in the formula of Compound III described above, Im represents $Im_1$, wherein $R_4$ is a methyl group, and $R_1$ represents a heptyl group.

14.2 mg of Compound (1) was dissolved into 1 mL of chloroform. 0.3 mL of a methanol solution saturated with zinc acetate was added to the mixture, and stirred for 30 minutes at room temperature. The mixture was washed with water and the solvent was evaporated to obtain 15.4 mg (yield: 100%) of the title compound. MS(TOF)m/e 1294.86 (M), Calc. 1294.57 (M); Ultraviolet-visible absorption spectrum (CHCl$_3$) $\lambda_{max}$410.5, 490.5, 584, 643 nm; Fluorescence spectrum (CHCl$_3$) $\lambda_{max}$664 nm($\lambda_{ext}$490 nm). Compound (3) in chloroform exists in the form of porphyrin array. Accordingly, the data of ultraviolet-visible absorption spectrum and fluorescent spectrum were obtained as the data of the poly(porphyrin) array.

3) Step 3

Synthesis of the porphyrin array 5(n)

Figure 1:
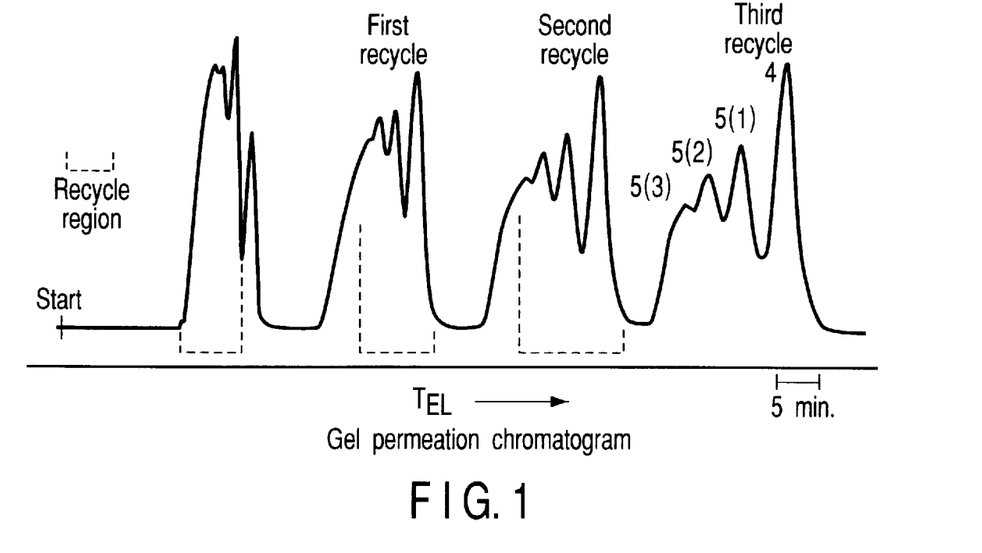
FIG. 1 is a gel permeation chromatogram of an example of a porphyrin array of the present invention.

2.5 μmol of Compound (2) and 7.7 μmol of Compound (3) were dissolved into 3 mL of pyridine, and the mixture was stirred for 30 minutes at room temperature. The solvent was removed by a vacuum pump and the remaining mixture was dried. Compound (4), Compound 5(1), Compound 5(2) and Compound 5(3) were separated with GPC. The obtained gel permeation chromatogram is shown in FIG. 1. 5(1): Visible absorption spectrum (CHCl$_3$) $\lambda_{max}$415, 477, 525, 580, 630, 655 nm; Fluorescence spectrum (CHCl$_3$) $\lambda_{max}$675 nm($\lambda_{ext}$415 nm); 5(2) :Visible absorption spectrum (CHCl$_3$) $\lambda_{max}$413, 483, 580, 640 nm; Fluorescence spectrum (CHCl$_3$) $\lambda_{max}$670 nm($\lambda_{ext}$413 nm); 5(3): Fluorescence spectrum (CHCl$_3$) $\lambda_{max}$413, 487, 525, 584, 640 nm; Fluorescence spectrum (CHCl$_3$) $\lambda_{max}$670 nm($\lambda_{ext}$413 nm)

4) Step 4

Synthesis of [5-(N-(5-methoxycarbonylpentyl)-N'-(2-ethyl)-pyromellitic diimide)-15-(1-methyl-2-imidazolyl)-10,20-bisheptyl]porphyrin (12)

126.5 mg (0.188 mmol) of N-(5-methoxycarbonylpentyl)-N'-(2-formylethyl)-pyromellitic diimide (9), 13.5 mg (0.113 mmol) of 1-methylimidazolyl-2-carbaldehyde (10), and 75.0 mg (0.300 mmol) of dipyrromethane 11) were dissolved in 24.0 mL of chloroform in a nitrogen atmosphere. 24 μL (0.300 mmol) of trifluoroacetic acid was added to the mixture, and stirred. After 30 minutes, 146.5 mg (0.600 mmol) of dichlorodicyanobenzoquinone was added, and stirred the mixture for 30 minutes. The mixture was washed with an aqueous solution saturated with sodium bicarbonate, and chloroform was evaporated.

After purification with silica gel column chromatography (the developing solvent: chloroform/acetone (10/1)), 4.1 mg (0.0615 mmol, yield: 4.5%) of the title compound was obtained. MS(TOF)m/e 958.13(M+1), calc. 958.17(M+1); $\lambda_{abs}$(CHCl$_3$) 418.5, 517.5, 552.5, 594.5, 651.0 nm; $^1$H NMR(δ:CDCl$_3$)–2.5(NH, s, 2H), 1.19–2.46(m, 34H), 3.30 (CH$_3$(im), s, 3H), 3.59–3.76(m, 7H), 4.88(CH$_2$, m, 4H), 5.11, (m, 2H), 7.39(im-4, s, 1H), 7.60(im-5, s, 1H), 8.16 (phenyl, s, 3H), 8.67(pyrrole, d, 2H), 9.37(pyrrole, d, 2H), 9.51(pyrrole, d, 2H), 9.63(pyrrole, d, 2H).

5) Step 5

Synthesis of [5-(N-(5-methoxycarbonylpentyl)-N'-(2-ethyl)-pyromellitic diimide)-15-(1-methyl-2-imidazolyl)-10,20-bisheptyl]porphyrin zinc complex (13)

4.1 mg (0.0615 mmol) of Compound (12) was dissolved into 5 mL of chloroform in a nitrogen atmosphere. 0.5 mL of a methanol solution saturated with zinc acetate was added to the chloroform solution, and the mixture was stirred for 2 hours. The organic layer was washed with 10 mL of distilled water, dried over magnesium sulfate anhydride, concentrated by an evaporator and purified with silica gel column chromatography (φ 1.5×10 cm, the eluent: chloroform), whereby 4.78 mg (0.0500 mmol, yield: 83%) of Compound 13 was obtained. The ultraviolet-visible absorption spectrum showing the split of the Soret band at 415.5 and 435.5 nm, and $^1$H NMR spectrum showing the high magnetic field shift of imidazole and pyrrole protons, indicate that Compound (13) has been coordination-organized and has a structure represented by the general formula (1-2). MS(TOF)m/e 1019.25(M+1), Calc. 1019.41 (M+1); $\lambda_{abs}$ (CHCl$_3$) 415.5, 435.5, 565.0, 622.0 nm; $^1$H NMR(δ:CDCl$_3$) 1.03 (CH$_3$, t, 6H), 1.39(CH$_3$, t, 3H), 1.79 (CH$_3$(im), s, 3H), 1.90(im-4, s, 1H), 1.50–1.70(CH$_2$, m), 2.00–2.10(CH$_2$, m, 4H), 2.35(CH$_2$COO, s, 2H), 2.78(CH$_2$, m(br), 2H), 2.94(CH$_2$, m(br), 2H), 3.64(N—CH$_2$, t, 2H), 3.68(OCH$_3$, s, 3H), 5.06(CH$_2$, (br), 6H), 5.38(pyrrole, d, 2H), 5.47(im-5, s, 1H), 5.56(CH$_2$, (br), 2H), 8.06(phenyl, s, 2H), 8.87 (pyrrole, d, 2H), 9.72(pyrrole, d, 2H), 9.93 (pyrrole, d, 2H).

The measurement results of the nonlinear optical property of the porphyrin array of the present invention, which had been synthesized in the aforementioned examples, were shown in Table 1. The structures of the reference compounds 6, 7 and 8(n) are shown below Table 1 (in the formula, $R_1$ and Im are heptyl and $Im_1$ ($R_4$=methyl), respectively. The reference compound 6 is a free base porphyrin as a monomer. The reference compound 7 is a zinc complex of the reference compound 6 and forms a dimer in chloroform by coordination bonds. The structure of the reference compound 8(n) is the same as that of the general formula (1-1) except that the substituents corresponding to $R_2$ and $R_3$ of the general formula (1-1) are both replaced by $R_1$.

TABLE 1

| | Third-order nonlinear optical property | | |
|---|---|---|---|
| Compound | \|γyyyy\| ($10^{-32}$ esu) | \|χ$^{(3)}$yyyy\| ($10^{-15}$ esu) | Concentration ($10^{-6}$ M) |
| 1 | 7 | 4 | 25 |
| 4 | 180 | 50 | 13 |
| 5 (1) | 950 | 165 | 8.3 |
| 5 (3) | 1300 | 163 | 5.0 |
| 6 | 14 | 91 | 320 |
| 7 | 8 | 24 | 150 |
| 8 (1) | 13 | 55 | 200 |
| 8 (2) | 61 | 38 | 30 |
| 8 (3) | 120 | 39 | 15 |

TABLE 1-continued

Third-order nonlinear optical property

| Compound | $|\gamma yyyy|$ ($10^{-32}$ esu) | $|\chi^{(3)} yyyy|$ ($10^{-15}$ esu) | Concentration ($10^{-6}$ M) |
|---|---|---|---|

6

7

8(n)
n = 1–3

Structures of reference compounds used in the measurements of nonlinear optical properties.

$\gamma_{yyyy}$ is the second-order hyper-polarizability, $\chi^{(3)}_{yyyy}$ is the third-order susceptibility. The values of $\gamma_{yyyy}$ of the arrays 7 and 8(n), which are constituted of only the zinc complexes, were in the range of $10^{-32}$ to $10^{-30}$ esu. The corresponding values of Compound 1 and Compound 6, which are free base porphyrin, were not so large as those of the arrays 7 and 8(n). On the other hand, only the arrays 4 and 5(n) of the present invention, in which the free base porphyrins, which serve as the acceptor, are bonded to the arrays of the zinc complexes, which serve as the donors, exhibit larger values in the range of $10^{-30}$ to $10^{-29}$ esu. The values are larger, by the order of one digit or so, than the corresponding values of the arrays 7 and 8(n) constituted of only the zinc complexes. That is, by combining a donor with an acceptor in the porphyrin array, the third-order nonlinear optical response has been remarkably enhanced. The method of producing a porphyrin array of the present invention enables easy introduction of a donor and an acceptor to the one-dimensional linear porphyrin array, which introduction has been difficult in the conventional method using connection by covalent bond.

6) Third-Order Nonlinear Optical Property

Figure 2:
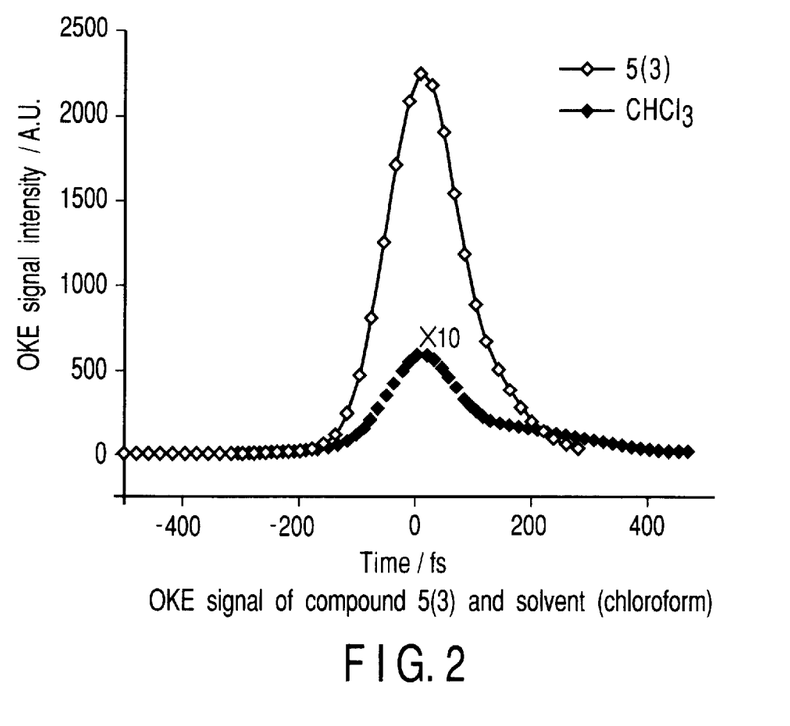
FIG. 2 is a graph which shows the OKE signal of the porphyrin array of the present invention and the OKE signal of chloroform.

In the measurement, a (Ti:sapphire) pulse laser having a time resolution of 150 femtoseconds was used in the chloroform solution and the signal intensity I of the Optical Kerr Effect (OKE) was measured. The OKE signal of Compound 5(3) and the OKE signal of the solvent (chloroform) alone are shown in FIG. 2.

The signal intensity I of formula 1 was assigned with the values of the signal intensity I of the OKE obtained as described above, whereby the third-order susceptibility $\chi^{(3)}$ was obtained. The subscript "Sample" represents a porphyrin compound and "Ref" represents the reference compound. The reference compound was carbon dioxide. "n" represents the refractive index of the solvent. As $\chi^{(3)}_{ref}$, the known value of third-order susceptibility was used (Opt. Lett. 1991, 16, 1683).

$$\left|\chi^{(3)}_{Sample}\right| = \left|\chi^{(3)}_{Ref}\right| \left(\frac{{}^nSample}{{}^nRef}\right)^2 \left(\frac{{}^ISample}{{}^IRef}\right)^{1/2} \quad (1)$$

The second-order hyper polarizability of the molecule (γ) was obtained by following formula 2.

$$\gamma = \frac{\chi^{(3)}_{Sample}}{NL} \quad (2)$$

wherein N represents the molecular density, and L is equal to $[(n^2+2)/3]^4$.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A porphyrin array having a third order nonlinear optical property represented by the following general formula (1-1) or (1-2):

(1-1)

(1-2)

wherein $R_1$ represents an alkyl group or a substituted or unsubstituted aryl group; $M_1$ represents a metal ion; $R_2$ and $R_3$ independently represent an electron acceptor or an electron donor; Im represents $Im_1$ or $Im_2$ set forth below:

wherein $R_4$ represents a hydrogen atom or a methyl group; and n represents an integer in the range of 1 to 100.

2. The porphyrin array according to claim 1, wherein the metal ion represented by $M_1$ is ion of a metal selected from a group consisting of zinc, iron, cobalt, ruthenium and gallium.

3. The porphyrin array according to claim 1, wherein the alkyl group represented by $R_1$ is an unsubstituted alkyl group having 1–20 carbon atoms, the unsubstituted aryl group represented by $R_1$ is a unsubstituted aryl group having 6–20 carbon atoms, and the substituted aryl group is an aryl group substituted with an alkyl group having a total of 7–30 carbon atoms or an aryl group substituted with an alkoxy group having a total of 7–30 carbon atoms.

4. The porphyrin array according to claim 1, wherein the electron acceptor represented by $R_2$ and $R_3$ is selected from the group consisting of free base porphyrin, gold porphyrin, pyromellitic diimide, dialkylviologen and benzoquinone, from all of which a hydrogen atom is removed to form a monovalent group, and the electron donor represented by $R_2$ and $R_3$ is ferrocene, from which a hydrogen atom is removed to form a monovalent group.

5. The porphyrin array according to claim 1, wherein $R_2$ and $R_3$ are independently selected from the group consisting of the following groups:

wherein $R_1$ and Im has the same meanings as defied in claim 1, $R_5$ and $R_7$ independently represent an alkylene group or arylene group; and $R_6$ and $R_8$ independently represent an alkyl group or aryl group.

6. The porphyrin array according to claim 1, wherein $R_2$ and $R_3$ independently represent a group selected from the group consisting of:

wherein $R_1$ and Im have the same meanings as defined in claim 1; $R_5$ represents an alkylene group or arylene group; and $R_6$ represents an alkyl group or aryl group.

7. A porphyrin derivative represented by the general formula (2-1) or (2-2):

(2-1)

(2-2)

wherein $R_1$ represents an alkyl group or a substituted or unsubstituted aryl group; $M_1$ represents a metal ion; $R_2$ and $R_3$ independently represent an electron acceptor or an electron donor; and Im represents $Im_1$ or $Im_2$ set forth below:

wherein $R_4$ represents a hydrogen atom or a methyl group.

8. The porphyrin derivative according to claim 7, wherein the metal ion represented by $M_1$ is ion of a metal selected from a group consisting of zinc, iron, cobalt, ruthenium and gallium.

9. The porphyrin array according to claim 7, wherein the alkyl group represented by $R_1$ is an unsubstituted alkyl group having 1–20 carbon atoms, the unsubstituted aryl group represented by $R_1$ is a unsubstituted aryl group having 6–20 carbon atoms, and the substituted aryl group is an aryl group substituted with an alkyl group having a total of 7–30 carbon atoms or an aryl group substituted with an alkoxy group having a total of 7–30 carbon atoms.

10. The porphyrin array according to claim 7, wherein the electron acceptor represented by $R_2$ and $R_3$ is selected from the group consisting of free base porphyrin, gold porphyrin, pyromellitic diimide, dialkylviologen and benzoquinone, from all of which a hydrogen atom is removed to form a monovalent group, and the electron donor represented by $R_2$ and $R_3$ is ferrocene, from which a hydrogen atom is removed to form a monovalent group.

11. The porphyrin array according to claim 7, wherein $R_2$ and $R_3$ are independently selected from the group consisting of the following groups:

-continued wherein $R_1$ and Im has the same meanings as defined in claim 7, $R_5$ and $R_7$ independently represent an alkylene group or arylene group; and $R_6$ and $R_8$ independently represent an alkyl group or aryl group.

12. The porphyrin array according to claim 7, wherein $R_2$ and $R_3$ independently represent a group selected from the group consisting of wherein $R_1$ and Im have the same meanings as defined in claim 7; $R_5$ represents an alkylene group or arylene group; and $R_6$ represents an alkyl group or aryl group.

13. A method of preparing a porphyrin array represented by formula (1-1) or (1-2):

(1-1)

(1-2)

wherein R$_1$ represents an alkyl group or a substituted or unsubstituted aryl group; M$_1$ represents a metal ion; R$_2$ and R$_3$ independently represent an electron acceptor or an electron donor; Im represents Im$_1$ or Im$_2$ set forth below:

wherein R$_4$ represents a hydrogen atom or a methyl group; and n represents an integer in the range of 1 to 100, comprising:
reacting, in the presence of a polar solvent, either one or both of porphyrin complexes represented by the general formulae (2-1) and (2-2):

(2-1)

-continued (2-2)

wherein $R_1$, $R_2$, $R_3$, $M_1$ and Im have the same meanings as in the general formula (1-1) with bis-porphyrin complex dimer represented by the general formula (3):

(3)

wherein $R_1$, $M_1$, Im have the same meanings as in the general formula (1-1); or reacting, in the presence of a polar solvent, either one or both of porphyrin complexes represented by the general formulae (2-1) and (2-2):

(2-1)

(2-2)

wherein $R_1$, $R_2$, $R_3$, $M_1$, and Im have the same meanings as in the general formula (1-1).

14. The method according to claim 13, wherein the metal ion represented by $M_1$ is ion of a metal selected from a group consisting of zinc, iron, cobalt, ruthenium and gallium.

15. The method according to claim 13, wherein the alkyl group represented by $R_1$ is an unsubstituted alkyl group having 1–20 carbon atoms, the unsubstituted aryl group represented by $R_1$ is a unsubstituted aryl group having 6–20 carbon atoms, and the substituted aryl group is an aryl group substituted with an alkyl group having a total of 7–30 carbon atoms or an aryl group substituted with an alkoxy group having a total of 7–30 carbon atoms.

16. The method according to claim 13, wherein the electron acceptor represented by $R_2$ and $R_3$ is selected from the group consisting of free base porphyrin, gold porphyrin, pyromellitic diimide, dialkylviologen and benzoquinone, from all of which a hydrogen atom is removed to form a monovalent group, and the electron donor represented by $R_2$ and $R_3$ is ferrocene, from which a hydrogen atom is removed to form a monovalent group.

17. The method according to claim 13, wherein $R_2$ and $R_3$ are independently selected from the group consisting of the following groups:

, and wherein $R_1$ and Im has the same meanings as defined in claim 13, $R_5$ and $R_7$ independently represent an alkylene group or arylene group; and $R_6$ and $R_8$ independently represent an alkyl group or aryl group.

18. The method according to claim 13, wherein $R_2$ and $R_3$ independently represent a group selected from the group consisting of wherein $R_1$ and Im have the same meanings as defined in claim 13, $R_5$ represents an alkylene group or arylene group; and $R_6$ represents an alkyl group or aryl group.

* * * * *